(12) United States Patent
Langhammer et al.

(10) Patent No.: US 9,658,157 B2
(45) Date of Patent: May 23, 2017

(54) SENSOR USING LOCALIZED SURFACE PLASMON RESONANCE (LSPR)

(75) Inventors: Christoph Langhammer, Göteborg (SE); Bengt Kasemo, Köpmannebro (SE); Igor Zoric, Angered (SE); Elin Larsson, Göteborg (SE)

(73) Assignee: Insplorion AB, Gothenburg (SE)

(*) Notice: Subject to any disclaimer, the term of this patent is extended or adjusted under 35 U.S.C. 154(b) by 140 days.

(21) Appl. No.: 13/261,045

(22) PCT Filed: May 25, 2010

(86) PCT No.: PCT/EP2010/057136
§ 371 (c)(1),
(2), (4) Date: Mar. 5, 2012

(87) PCT Pub. No.: WO2010/136440
PCT Pub. Date: Dec. 2, 2010

(65) Prior Publication Data
US 2012/0188551 A1 Jul. 26, 2012

(30) Foreign Application Priority Data
May 25, 2009 (SE) ...................... 0950368

(51) Int. Cl.
*G01N 21/55* (2014.01)
*G01N 21/552* (2014.01)
*G01N 21/65* (2006.01)

(52) U.S. Cl.
CPC ......... *G01N 21/554* (2013.01); *G01N 21/658* (2013.01)

(58) Field of Classification Search
CPC ......... G01N 21/55; G01N 33/53; G01N 11/00
USPC ................ 356/445; 435/5, 7.1; 73/53.01; 136/257, 201; 257/316; 324/204
See application file for complete search history.

(56) References Cited

U.S. PATENT DOCUMENTS

| | | | |
|---|---|---|---|
| 2005/0035757 A1* | 2/2005 | Prins et al. | 324/204 |
| 2005/0087000 A1* | 4/2005 | Coehoorn et al. | 73/53.01 |
| 2007/0248987 A1* | 10/2007 | Imamura et al. | 435/7.1 |

(Continued)

FOREIGN PATENT DOCUMENTS

WO  WO 2008/039140 A1  4/2008

OTHER PUBLICATIONS

Jensen, TR et al., 2000, Nanosphere Lithography: Tunable Localized Surface Plasmon Resonance Spectra of Silver Nanoparticles, J. Phys. Chem. 104:10549-556.

(Continued)

*Primary Examiner* — Tarifur Chowdhury
*Assistant Examiner* — Jamil Ahmed
(74) *Attorney, Agent, or Firm* — Lynn E. Barber (57) ABSTRACT

The invention concerns an arrangement comprising at least one sensor nanoparticle supporting Localized Surface Plasmon Resonance (LSPR), at least one sensing material and at least one separating layer which separates the at least one sensor nanoparticle from the at least one sensing material. The arrangement allows for indirect sensing studies of change in and on the surface of a sensing material or environment by the sensor nanoparticle. The arrangement may also be used for optical temperature measurements and calorimetry, optical differential scanning calorimetry (DSC), to study hydrogen storage, catalytic reactions or for NOx sensing.

16 Claims, 10 Drawing Sheets

(56) References Cited

U.S. PATENT DOCUMENTS

| | | | |
|---|---|---|---|
| 2008/0246076 A1* | 10/2008 | Chen | 257/316 |
| 2009/0107535 A1* | 4/2009 | Hu | 136/201 |
| 2009/0250110 A1* | 10/2009 | Yu et al. | 136/257 |
| 2012/0208174 A1* | 8/2012 | Galush et al. | 435/5 |

OTHER PUBLICATIONS

Jonsson, MP et al., 2007, Supported Lipid Bilayer Formation and Lipid-Membrane-Mediated Biorecognition Reactions Studied with a New Nanoplasmonic . . . Nano Letters 7(11): 3462-68.

Langhammar, C. et al., 2007, Absorption and scattering of light by Pt, Pd, Ag, and Au nanodisks: Absolute cross sections and branchi . . . , J. Chem. Phys. 126: 194702-1-194702-11.

Langhammar, C. et al., 2008, Localized Surface Plasmon Resonances in Aluminum Nanodisks, Nano Lett. 8(5): 1461-1471.

McFarland, A. et al., 2003, Single Silver Nanoparticles as Real-Time Optical Sensors with Zeptomole Sensitivity, Nano Lett. 3(8): 1057-1062.

Murray, WA et al, 2006, Overlayers on Silver Nanotriangles: Field Confinement and Spectral Position of Localized Surface Plasmon . . . , Nano Lett. 6(8): 1771-1777.

Rindzevicius, T. et al., 2007, Long-Range Refractive Index Sensing Using Plasmonic Nanostructures, J. Phys. Chem. 111: 11806-11810.

Willets, KA et al., 2007, Localized Surface Plasmon Resonance Spectroscopy and Sensing, Annu. Rev. Phys. Chem. 58: 267-97.

Zheng, YB et al., 2008, Active Plasmonic Devices Based on Ordered Au Nanodisk Arrays, MEMS, Tucson, AZ, USA, Jan. 13-17, 2008.

\* cited by examiner

SENSOR USING LOCALIZED SURFACE PLASMON RESONANCE (LSPR)

CROSS-REFERENCE TO RELATED APPLICATIONS

This patent application claims priority from PCT/EP2010/057136 filed 25 May 2010, which claims priority from SE 0950368-1 filed 25 May 2009.

TECHNICAL FIELD

The present invention relates to an arrangement comprising nanoparticles for sensing. More specifically, the present invention relates to an arrangement comprising nanoparticles supporting localized surface plasmon resonances and a sensing material, which are separated from each other by a separating layer. Further, the present invention relates to a system comprising such an arrangement.

BACKGROUND OF THE INVENTION

The development of novel techniques to study processes and phenomena at the nanoscale is of fundamental importance for nanoscience and nanotechnology. Only by fully understanding nanoscale processes and the physics and materials science of nanoparticles and nanostructures, can nanotechnological solutions be applied widely, with appropriate risk management. The heart of the anticipated technological advances through "nanotechnology" is the wide range of novel physical and chemical properties of nanoparticles and nanostructures. The typical size range of nanoparticles/nanostructures used to define nanotechnology is 1—a few hundred nanometers (nm), the exact upper boundary depending on the property studied and the application in mind. These novel exciting properties of nanoparticle systems can be advantageous in the development of both novel sensors and scientific tools to characterize and learn more about the physics and materials science of nanoparticle systems, as well as in developing new technologies for applications in biotechnology, medicine, clean tech, engineering, etc.

An inherent feature of metallic nanoparticles is a collective coherent oscillation of the conduction electrons—the localized surface plasmon resonance (LSPR), which can be excited by external photons. In other words, the LSPR is a possible excited state of the metal nanoparticle electron system, which can be excited by photons or, equivalent^, by the electromagnetic field of light incident on the particle. The LSPR excitation is a consequence of the inter-electronic (collective) interactions of the electrons combined with spatial confinement of the conduction band electron system within the nanoparticle volume. An electron density wave is formed with a frequency/wavelength/energy that depends on the electronic structure of the nanoparticle, its geometry, size and dielectric environment.

The spectral sensitivity of the LSPR, that is the amount of spectral shift of the LSPR along the wavelength/frequency/energy axis (alternatively, a spectral sensitivity of a LSPR is also measurable in terms of a change of the peak height, the peak full-width-at-half-maximum (FWHM) or also as a change in the optical extinction or transmission spectrally close to the LSPR frequency), to events taking place on the surface of and close to the nanoparticles opens up the possibility to use "plasmonic" nanoparticles as transducers in sensors in general, where applications as biosensors have been most exploited so far. "Events" in the preceding sentence are e.g. refractive index changes in the surrounding medium induced by adsorption of biomolecules onto the nanoparticle surface. Most of these reported applications of LSPR in plasmonic biosensors rely on the sensitivity of the nanoparticle LSPR to the dielectric constant of the surrounding medium, opening up a route to "refractive index sensing" where adsorbate-induced changes in the local dielectric environment are utilized for detection of e.g. molecular binding events on the nanoparticle surface and in the particle nano-environment. In a typical nanoplasmonic refractive index sensor the events to be detected take place directly on the surface of e.g. plasmonically active gold nanoparticles. This is motivated by the strong enhancement of the electric field in the close (<ca. 50 nm, depending on particle size and material and geometry) proximity of the nanoparticle surface. During the actual sensing, a change of the local refractive index at the interface between nanoparticle and surrounding medium, induced by e.g. adsorption or chemical binding of molecules from solution to the sensor nanoparticle surface, is detected as a change of the particle's optical response.

In addition, nano-LSPR sensors open up the possibility for miniaturization because of the small size of the transducers i.e. the plasmonic nanoparticles. Another related advantage is the small detection volume making it possible to measure extremely small amounts of analytes. Due to their small size, nanoscale sensors offer the potential for multiplexing (i.e. making sensor arrays where each sensor has a different sensitivity). One application of multiplexing is fingerprinting, where a large number of sensors with slightly different sensitivities, are used in a sensor array. Even if the specificity and selectivity of each individual sensor may be low and not very informative alone, the combined response from all sensors can, using pattern recognition, provide a highly accurate and informative response.

Many different nanoparticle shapes have been investigated for their potential use in plasmonic refractive index (bio-) sensors, including disks, triangles, rods, ellipses, wires, spheres, cubes, stars, holes in a thin metal film, nanoshells and core-shell particles, nanorice and nanorings.

Plasmonic refractive index sensing platforms comprising a nanoparticle based sensing structure, exhibiting and relying on a confined optical excitation like LSPR are previously known.

As an alternative to plasmonic refractive index sensing it has also been shown that by using a "direct sensing" approach one is able to measure an induced structural (e.g. size and/or geometry) change and a change of the electronic structure of a plasmonic nanoparticle upon absorption of atoms into the plasmonic nanoparticle. In particular, this approach has been demonstrated for measurements of hydrogen uptake in Pd nanoparticles. Thus, during a direct sensing event, the sensor nanoparticles themselves are affected/changed by the process to be sensed. The latter process may ultimately lead to altered physical properties of the nanoparticles and give rise to a (measured) change of their optical response, i.e. their LSPR. Typically, the event to be sensed induces a spectral shift and/or a change of the spectral linewidth and/or the optical cross-section of the measured optical excitation of the nanoparticle. This can be detected as a significant altering of the optical transmission and/or extinction and/or absorption and/or scattering and/or reflection signature of the nanoparticle.

SUMMARY OF THE INVENTION

It is an objective of the present invention to provide an improved arrangement for sensing.

The present invention provides an arrangement, which addresses problems of known sensing platforms and at the same time provides further measurement possibilities.

In a first aspect of the invention there is provided an arrangement which is primarily characterized by at least one sensor nanoparticle supporting localized surface plasmon resonance (LSPR), at least one sensing material and at least one separating layer which separates the at least one sensor nanoparticle from the at least one sensing material.

In this document, the term nanoparticle shall be understood to mean particles having at least one dimension equal to or less than 500 nm, preferably equal to or less than 300 nm, more preferably equal to or less than 100 nm.

Thus, the arrangement comprises (i) at least one sensor nanoparticle that is plasmonically active (ii) a material, hereinafter denominated sensing material, which undergoes some change upon interaction with the surrounding medium or upon heating and cooling and (iii) a thin layer separating the optically active sensor nanoparticle(s) from the medium/environment and from the sensing material. Said thin layer is hereinafter denominated separating layer. By plasmonically or optically active sensor nanoparticle is understood that the nanoparticle supports a localized surface plasmon resonance.

The arrangement according to the present invention provides for indirect sensing of a medium or environment. By indirect sensing is understood that the sensor nanoparticle is separated from the environment and the sensing material by a separating layer.

It is to be understood that the sensing material interacts with or undergoes a change due to the temperature, the medium or environment it is exposed to. Further, it is to be understood that the optically active sensor nanoparticle(s) do not interact with or undergo a change themselves due to changes in the sensing material or due to the medium or environment to be sensed. The exception is the monitoring of electric charging and discharging of the of the sensor nanoparticle(s), for example by electron transfer during a chemical reaction, or of temperature changes caused by, for example, an exothermic/endothermic reaction on/of the sensing material. The latter temperature change causes a volume and electronic change in the sensor nanoparticles, which can be detected as a change in the optical response. The arrangement according to the invention may be used to measure, at ultra-high sensitivity, an induced structural, chemical and/or electronic change in a sensing material or a temperature change caused by, for example, a chemical/catalytic reaction on/of the sensing material or by a phase transition in/of the sensing material or by a temperature change in the surrounding medium. The sensing material includes nanoparticles, thin films or a bulk material made from a solid, a liquid, soft matter or a gas. The induced change is detected as a change in the optical response of the optically active sensor nanoparticle(s) by reading out the altered optical response of said sensor nanoparticle(s). This is in contrast to the previously known refractive index sensing and direct sensing where the sensor nanoparticle is in direct contact with the surrounding medium/environment and the entities to be sensed or itself undergoes a structural or electronic or chemical change during the sensing event, respectively.

As readout signal to monitor changes in the LSPR excitations of the sensor, the spectral LSPR-peak shift (in extinction, scattering or absorption) along the wavelength/frequency/energy axis or the change of the peak height, the peak spectral line-width, the peak full-width-at-half-maximum (fwhm) or also the change in optical extinction/scattering/absorption or transmission at or spectrally close to the LSPR peak can be used.

The readout signal can also be a Surface Enhanced Raman Scattering (SERS) or Surface Enhanced Infrared Absorption Spectroscopy (SEIRAS) signal.

Surprisingly, it has been found that the ultrahigh sensitivity of previously known LSPR based sensors is maintained in the arrangement according to the present invention despite the introduction of a separating layer, which prohibits the placement of the sensing material directly onto the sensor particle itself, where the optical field enhancement and thus the sensitivity is expected to be largest. This construction, with separating layer, allows the operation of such a device in harsh environments, at high temperatures, in oxidizing/reducing atmospheres and with material combinations otherwise not possible (because of intermixing like e.g. alloy formation) since the optically active sensor nanoparticle(s) is/are physically protected and separated from the sensing material. Thus, in contrast to previously known refractive index and direct sensing, where the sensor nanoparticle sustaining LSPRs is exposed directly to the sensing environment, the arrangement according to the present invention separates the optically active sensor nanoparticle from the sensing material which in many cases is advantageous. Specific advantages of the present invention are: remote character of optical sensing, real time measurements, possibility of using transmission or reflection measurements for, in principle, simple detection of complex processes, as well as the potential for multiplexing (fingerprinting) and rapid material screening. One specific advantage of the present invention is its versatility since basically any material can be applied onto the separating layer that is protecting the sensor nanoparticle(s) from reacting with the sensing material. The latter separating layer also physically protects the sensor nanoparticle(s) in harsh environments from the harsh environment. Furthermore the separating layer provides i) a means to tailor the surface chemistry (since it can be chosen freely as long as it is non-metallic) of the sensor, and can in that role ii) be either an inert substrate for the nanomaterials to be studied, or iii) participate actively in the process under study, e.g spillover effects from a supported nanocatalyst.

While the particle size and shape and dielectric properties of the nanoparticle is quite restricted in the case of direct sensing where the sensor nanoparticle also constitutes the sensing material (i.e. has to be a nanoparticle supporting some optical excitation), there are almost no such restrictions for sensor nanoparticles of arrangements according to the present invention. For example, one can with the latter approach sense changes even in a continuous medium (like thin film) or in particles that do not sustain LSPR at all or are too small to sustain LSPR in the visible spectral range.

Furthermore and surprisingly LSPR can also be used to remotely and in real time measure the local temperature at the nanoscale by making use of the intrinsic temperature sensitivity of the LSPR excitation. In that way LSPR can be exploited as a nano-thermometer and provides an optical nano-calorimetric way of studying e.g. catalytic and chemical reactions or phase transitions. In other words, by calibrating the T-dependence of the LSPR sensor beforehand one obtains a sensitive nano-thermometer, capable of measuring very local temperature changes of and/or close to the plasmonic sensor nanoparticles in the sensing material and/or the surrounding medium. The general concept of this optical nano-calorimetry is directly extendable to common materials science techniques like e.g. differential scanning calorimetry (DSC) and may allow local DSC measurements at the nanoscale with extremely small sample material amounts or even on single nanoparticles.

However, it should be appreciated that for the use as an optical nano-thermometer the presence of a separating layer and a sensing material are not strictly necessary, i.e. temperature can be measured in a "direct sensing" approach with bare metallic sensor nanoparticle(s). The latter may be an attractive solution in few applications (e.g. in ultra high vacuum). For most applications, however, where the sensor nanoparticle(s) are exposed to a surrounding medium a separating layer with a predominantly protective function is an advantage since it prevents structural reshaping of the sensor nanoparticles, abrasion, fouling. Furthermore, on most metallic sensor nanoparticles a native, for example, oxide layer acting as separating layer is immediately formed upon exposure to ambient conditions.

In a second aspect of the invention there is provided an arrangement according to any previous aspect of the invention, wherein the at least one sensor nanoparticle exhibits a change of its LSPR upon a structural, chemical, refractive index, temperature and/or electronic change of said sensing material and/or surrounding medium.

An exothermic/endothermic chemical/catalytic reaction on/with the sensing material or a phase transition in/on the sensing material may cause a temperature change of the sensing material and/or the sensor nanoparticle(s) resulting in a change of the LSPR response of the at least one sensor nanoparticle.

In a third aspect of the invention there is provided an arrangement according to any previous aspect of the invention, wherein the at least one sensor nanoparticle exhibits a change of its LSPR response upon a temperature change of the surrounding medium, and/or the sensing material and/or the at least one sensor nanoparticle.

In a fourth aspect of the invention there is provided an arrangement according to any previous aspect of the invention, wherein the change of the optical response is a spectral shift of the LSPR, a change of optical cross section such as extinction, absorbance, transmission, absorption, scattering or reflection, a change of spectral line width and/or a change of the optical cross-section spectrally close to the LSPR.

The optically active sensor nanoparticle(s) may be of arbitrary shape provided that it (they) support(s) LSPR. The sensor nanoparticles may be the same or different. The readout of the optically active sensor nanoparticles may be either optical or electronic.

In a further aspect of the invention there is provided an arrangement according to any previous aspect of the invention, wherein said at least one sensor nanoparticle is a rod, wire, ellipse, polygon, disk, triangle, sphere, cube, star, hole in thin metal films, nanoshell, core-shell particle, nanorice or nanorings. The sensor nanoparticles may be the same or different.

In a further aspect of the invention there is provided an arrangement according to any previous aspect of the invention, wherein the at least said one sensor nanoparticle comprises a metal.

In a further aspect of the invention there is provided an arrangement according to any previous aspect of the invention, wherein said metal is selected from Ag, Au, Cu, Al, Mg, Ni, Sn, Hf, Ru, Rh, Ir, Cr, Pd and Pt.

The sensing material may be the same material as the separating layer. In this case the separating layer is the part of the material that is closest to the optically active sensor nanoparticles, which does not undergo any change during the sensing event. However, it should be appreciated that it is very difficult to actually draw a strict boundary between active and inactive parts of the material. Further, nanoparticles functioning as a catalyst may be placed on the sensing material. The sensing material may also, more generally, be of a different material than the separating layer.

The change in the sensing material detected by the optically active sensor nanoparticle(s) may be caused by a "reaction". A "reaction" may (i) be a chemical reaction that takes place at the interface between the surrounding gas or liquid or solid phase and the sensing material. If the reaction is a chemical reaction it may e.g. be dissociation, chemisorption, physisorption, the formation of one/several new compound(s) on/within the sensing material. The "reaction" can (ii) also be a phase transition, which is taking place on and/or within the sensing material. The change in the sensing material detected by the optically active sensor nanoparticle(s) caused by the "reaction" can be a change in refractive index, or near field coupling between the optically active sensor nanoparticle's optical excitation and the sensing material, or a change of shape/size of the sensing material, or electron and/or hole transfer between the sensor nanoparticle(s) and the sensing material or a combination of those. Furthermore the reaction on/in the sensing material may induce an electronic/chemical change in the separating layer, which is detected by the sensor nanoparticles.

In a further aspect of the invention there is provided an arrangement according to any previous aspect of the invention, wherein said sensing material is in the form of particles, nanoparticles, nanowires, nanofibres, nanotubes, a thin film and/or bulk material in solid, liquid, or gas phase.

All of the preceding aspects may also be used with any claims, aspects or embodiments of the invention hereinbefore or hereinafter.

In a further aspect of the invention there is provided an arrangement according to any previous aspect of the invention, wherein said separating layer is selected from transition metal oxides, sulfides, nitrides, carbides, alkaline earth metal oxides and hydrogels.

In a further aspect of the invention there is provided an arrangement according to any previous aspect of the invention, wherein said separating layer is a solid or a liquid.

In a further aspect of the invention there is provided an arrangement according to any previous aspect of the invention, wherein said separating layer is made of a metal oxide such as aluminum oxide $Al_2O_3$, magnesium oxide MgO, beryllium oxide BeO, barium oxide BaO, cerium oxide CeO, $Ce_2O_3$, semiconductor oxides such as silicon dioxide $SiO_2$; insulators, carbides, nitrides, sulfides, and polymers such as poly(hydrogenmethylsiloxane) PHMS, Poly(dimethylsiloxane) PDMS or Poly(methylmethacrylate) PMMA.

The separating layer may be any film that is thin enough (typically less than 1000 nm) to allow that a change in the sensing material is optically sensed by the optically active sensor nanoparticles.

In a further aspect of the invention there is provided an arrangement according to any previous aspect of the invention, wherein said separating layer has a thickness that is equal to or less than 1000 nm, 0.25-1000 nm, 400-1000 nm, 75-500 nm, 10-100 nm, and 5-50 nm or 0.25-10 nm.

The optically active sensor nanoparticle(s) can either be dispersed in soft matter or solid matter or located on a substrate. If the optically active sensor nanoparticle(s) is deposited onto a substrate, the latter is not considered as a separating layer and may either be inert (i.e. not participating in the reaction) or chemically active and participate in the reaction.

In a further aspect of the invention there is provided an arrangement according to any previous aspect of the invention, wherein said arrangement is located on a substrate or dispersed in soft or solid matter. Examples of soft or solid matter include, but are not limited to, water, organic solvents, lipids, hydrogels or liquid crystals and oxides, nitrides, carbides, metal oxides, glasses, fused silica or semiconductors, respectively.

The invention may be used in a system for measuring different chemical and/or physical and/or mechanical characteristics. Said system comprises control and measurement electronics, computational devices (such as a personal computer (PC)), and physical detectors (e.g. optical detectors, electron detectors, particle detectors, and so on).

In a further aspect of the invention there is provided a system comprising the arrangement according to any previous aspect of the invention further comprising control and measurement electronics, computational devices and/or physical detectors.

The present invention may be used in a variety of applications including humidity sensors, temperature sensors, hydrogen sensors, characterization of hydrogen storage material, car exhaust gas sensors (e.g. nitric oxides $NO_x$, carbon oxides $CO_x$, sulfur oxides $SO_x$, wherein x is 0.5, 1, 2, 3 or 4), catalysis/catalytic reaction sensors and optical calorimeters or optical differential scanning calorimeters (DSC).

An arrangement according to any previous aspect, wherein said structural, chemical, refractive index, and/or electronic change of said sensing material is caused by hydrogen absorption/desorption, $NO_x$ storage and/or a chemical/catalytic reaction.

In a further aspect of the invention there is provided the use of an arrangement or system according to any previous aspect of the invention for hydrogen storage, catalytic reaction sensing or $NO_x$ sensing. $NO_x$ is a collective name for NO, $NO_2$ and $N_2O$.

In a further aspect of the invention there is provided the use of an arrangement or system according to any previous aspect of the invention for surface enhanced Raman scattering spectroscopy (SERS) and/or surface enhanced infrared absorption spectroscopy (SEIRAS).

All of the preceding aspects may also be used with any claims, aspects or embodiments of the invention hereinbefore or hereinafter.

BRIEF DESCRIPTION OF THE DRAWINGS

In the following, the invention is described more closely with reference to the enclosed Figures.

DETAILED DESCRIPTION OF PREFERRED EMBODIMENTS

Figure 1A:
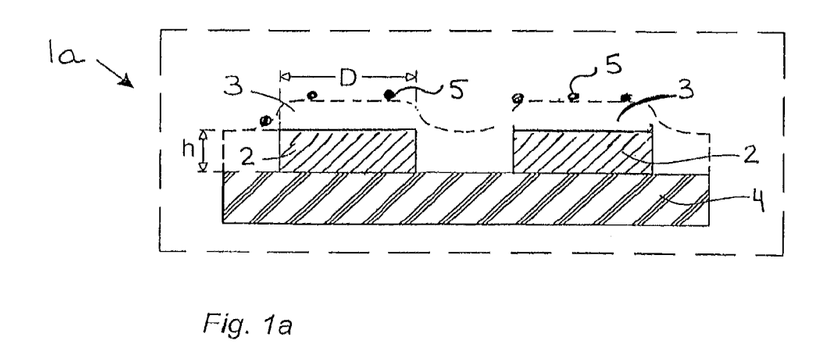
FIG. 1a is a sectional view of an arrangement according to the invention.

FIG. 1a is a sectional view of an arrangement 1a according to the invention in which circular nanodisks 2 having a diameter D and a height h are placed on a substrate 4. The nanodisks are covered by a separating layer 3. A sensing material in the form of nanoparticles 5 is placed on the separating layer. In one specific embodiment the nanodisk 2 is made of Au, the separating layer is $SiO_2$ and the nanoparticles 5 are made of palladium. In another embodiment the nanodisk is made of Au, the separating layer is made of BaO and the nanoparticles 5 are made of platinum. In still a further embodiment the circular nanodisk 2 is made of gold and has a diameter D=76 nm and a height h=30 nm, the separating layer is $SiO_2$ and has a thickness of 10 nm, the sensing material is platinum nanoparticles having a diameter of about 12 nm, and the substrate is made of glass.

Figure 1B:
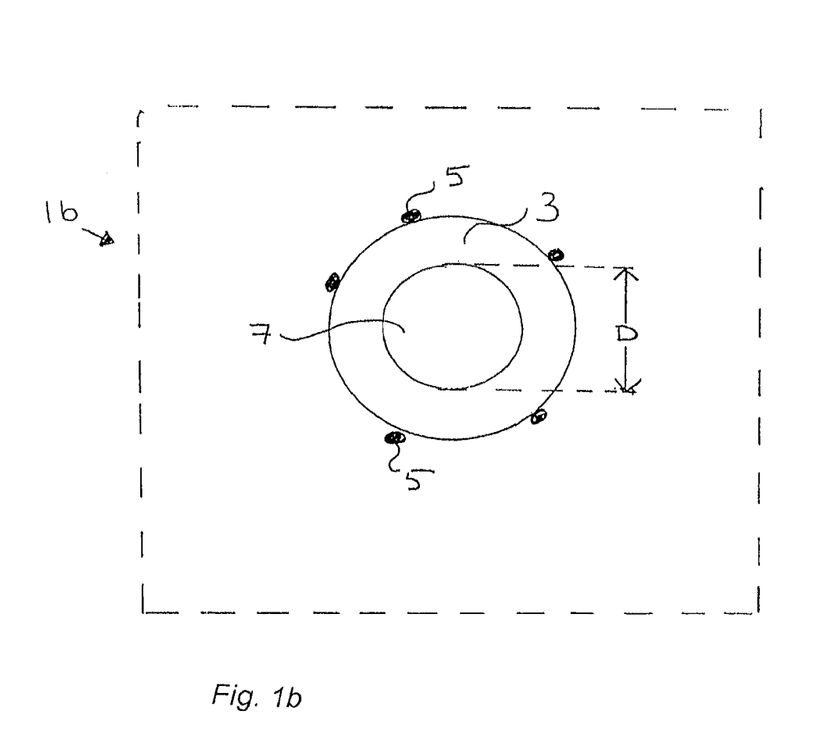
FIG. 1b is a sectional view of an arrangement according to the invention.

FIG. 1b is a sectional view of an assembly 1b of an arrangement according to the invention in which spherical nanoparticles 7 having a diameter D are covered by a separating layer 3. A sensing material in the form of nanoparticles 5 is placed on the separating layer. The arrangement 1b may be dispersed in soft or solid matter.

Figure 2A:
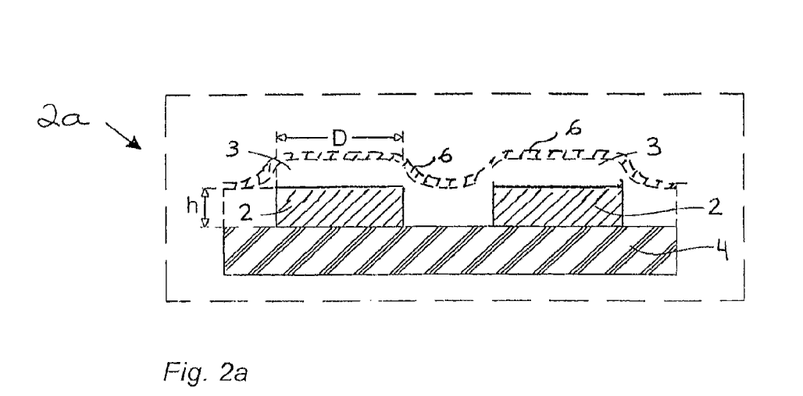
FIG. 2a is a sectional view of an arrangement according to the invention.

FIG. 2a is a sectional view of an arrangement 2a according to the invention in which circular nanodisks 2 having a diameter D and a height h are placed on a substrate 4. The nanodisks are covered by a separating layer 3. A sensing material in the form of a layer 6 is placed on the separating layer on the opposite side of the separating layer 3 from the nanodisks 2. The layer 6 may be made of the same or a different material as the separating layer 3. In one embodiment of the invention the nanodisk is made of Au, the separating layer is made of BaO and the layer 6 is made of BaO.

Figure 2B:
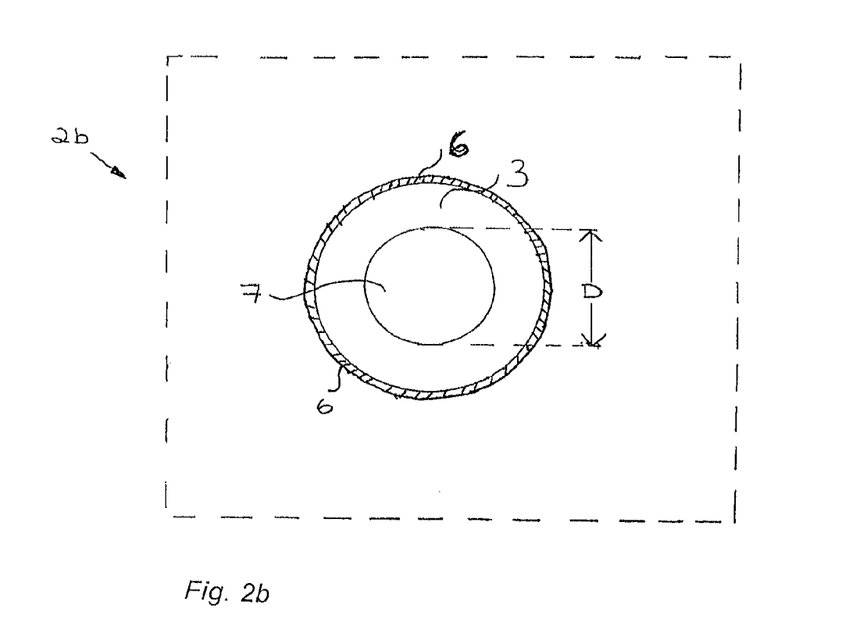
FIG. 2b is a sectional view of an arrangement according to the invention.

FIG. 2b is a sectional view of an assembly 2b of an arrangement according to the invention in which spherical nanoparticles 7 having a diameter D are covered by a separating layer 3. A sensing material in the form of a layer 6 is placed on the separating layer. The layer 6 may be made of the same or a different material as the separating layer 3. The arrangement 2b may be dispersed in soft or solid matter.

Figure 3:
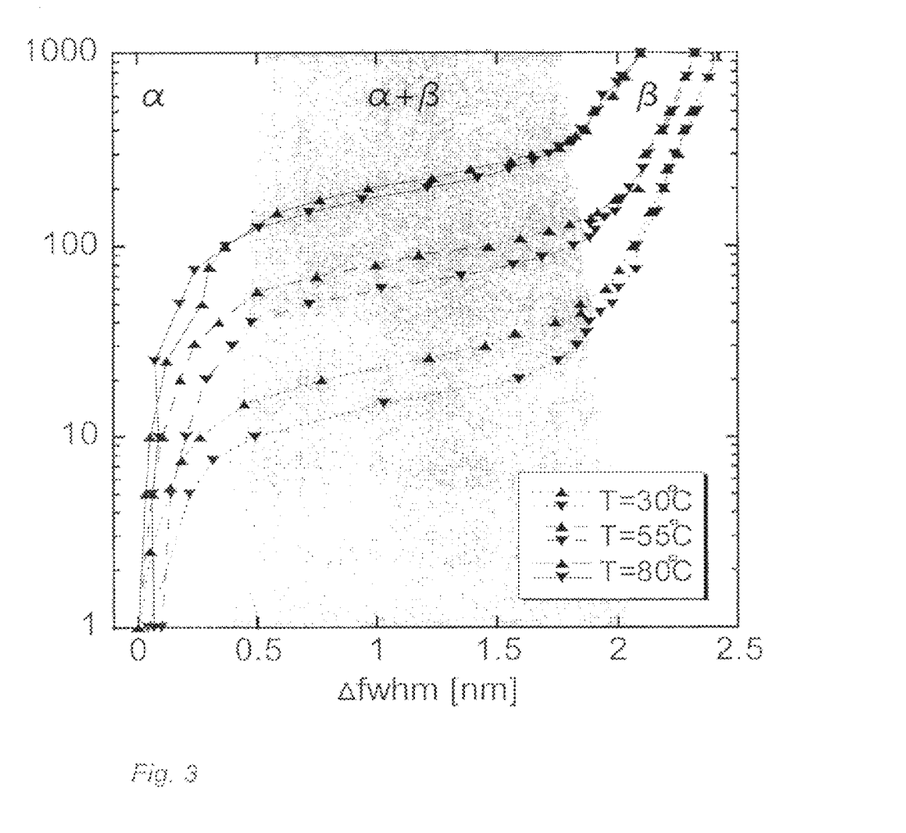
FIG. 3 is a graph showing LSPR hydrogen absorption and desorption isotherms.

FIG. 3 is a graph showing LSPR hydrogen absorption and desorption isotherms. Triangles pointing up and down are used to symbolize hydrogen absorption and desorption, respectively. The shift if the LSPR peak full-width-at-half maximum ($\Delta$fwhm, in nm) is shown as a function of time when the arrangement of the invention was exposed to step-wise increasing and decreasing $H_2$-gas pressure. More information about FIG. 3 is provided in the Examples.

Figure 4:
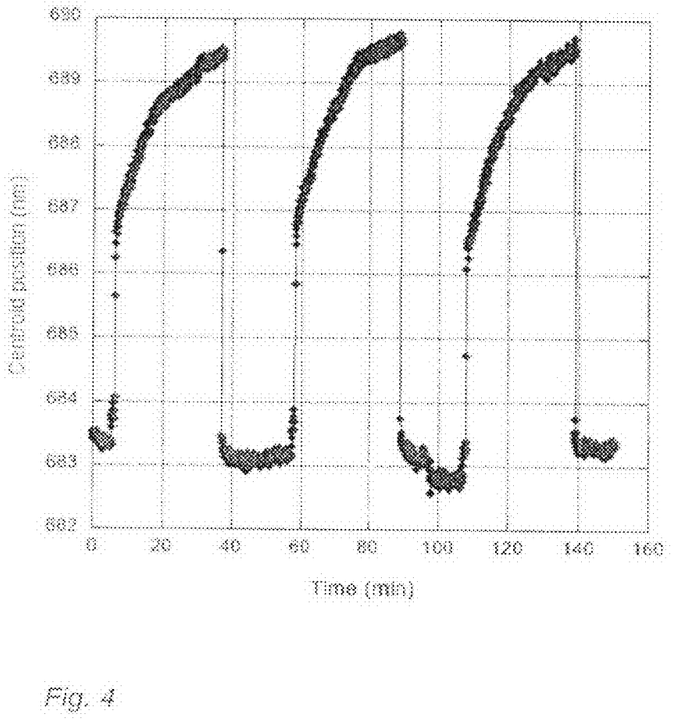
FIG. 4 is a graph showing the shift in the LSPR peak position (in nm) as a function of time when an arrangement according to the invention was exposed to periodic pulses of $NO_x$ and $H_2$.

FIG. 4 is a graph showing the shift in the LSPR peak position (in nm) as a function of time when an arrangement according to the invention was exposed to periodic pulses of $NO_x+O_2$ and $H_2$. More information about FIG. 4 is provided in the Examples.

Figure 5A:
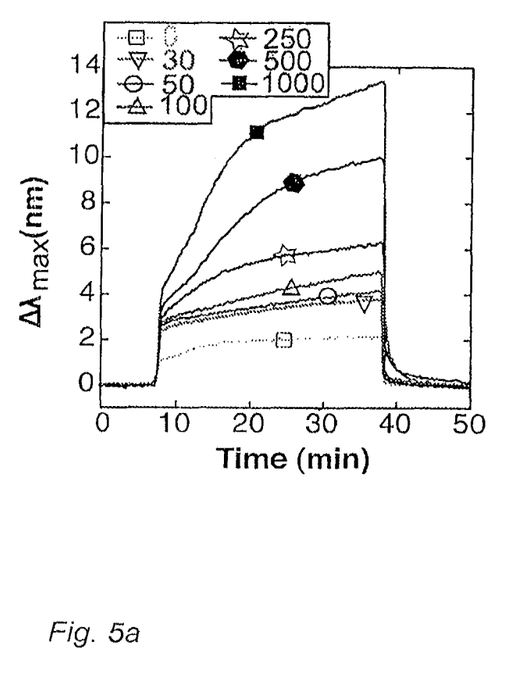
FIG. 5a is a graph showing the LSPR peak shift as a function of $NO_2$ concentration in the gas feedstock.

FIG. 5a is a graph showing the LSPR peak shift as a function of $NO_2$ concentration in a gas feedstock. More information about FIG. 5a is provided in the Examples.

Figure 5B:
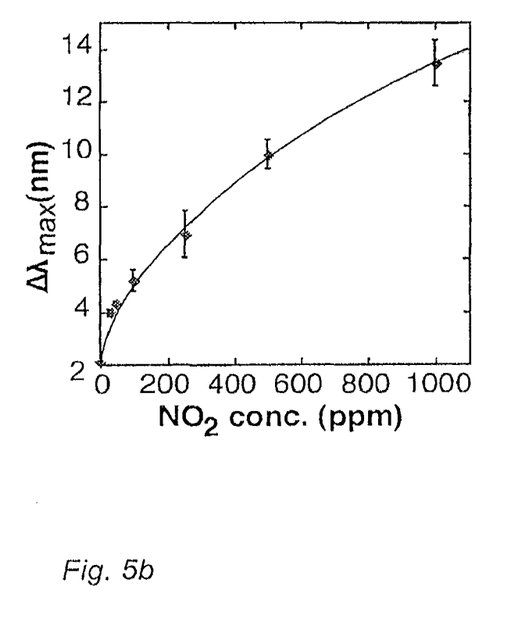
FIG. 5b is a graph showing a calibration curve obtained by plotting the peak value of the LSPR shift versus $NO_2$ concentration in the feed flow.

FIG. 5b is a graph showing a calibration curve obtained by plotting the peak value of the LSPR shift versus $NO_2$ concentration in a feed flow. More information about FIG. 5b is provided in the Examples.

Figure 6:
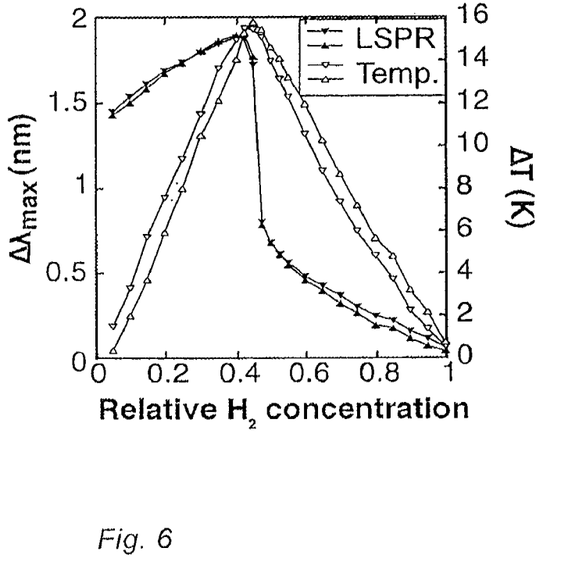
FIG. 6 is a graph showing the LSPR peak shift and temperature variation during scans of the reactant concentration ($\alpha$).

FIG. 6 is a graph showing the LSPR peak shift ($\Delta\lambda_{max}$) and temperature variation during scans of the reactant concentration ($\alpha$). Triangles pointing up and down are used to symbolize sweeps with increasing and decreasing relative $H_2$ concentration, respectively. The step in $\Delta\lambda_{max}$ illustrates the change in surface coverage upon passing the kinetic phase transition. To the left of $\Delta\lambda_{max}$ the sensing material is covered by oxygen. To the right of $\Delta\lambda_{max}$ the sensing material is covered by hydrogen. More information about FIG. 6 is provided in the Examples.

Figure 7:
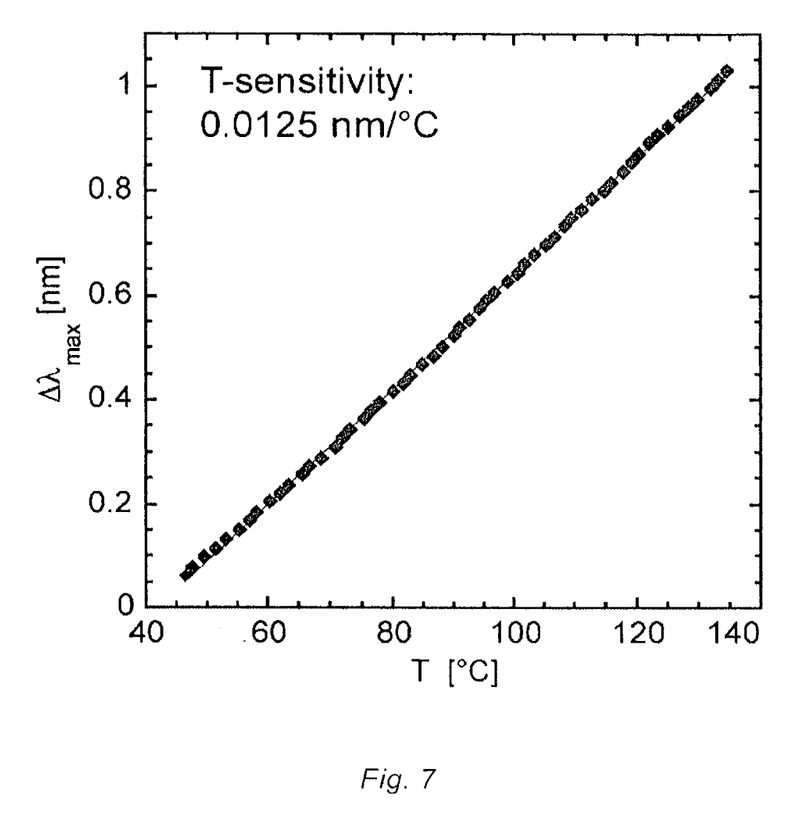
FIG. 7 is a graph showing the temperature dependence of the Au sensor nanodisk LSPR peak.

FIG. 7 is a graph showing the temperature dependence of the Au sensor nanodisk LSPR peak. This curve can be used as a calibration curve to e.g. measure a local temperature rise in the sensor caused by e.g. an exothermic catalytic reaction. In this way a nano-calorimetric measurement can be established.

Figure 8:
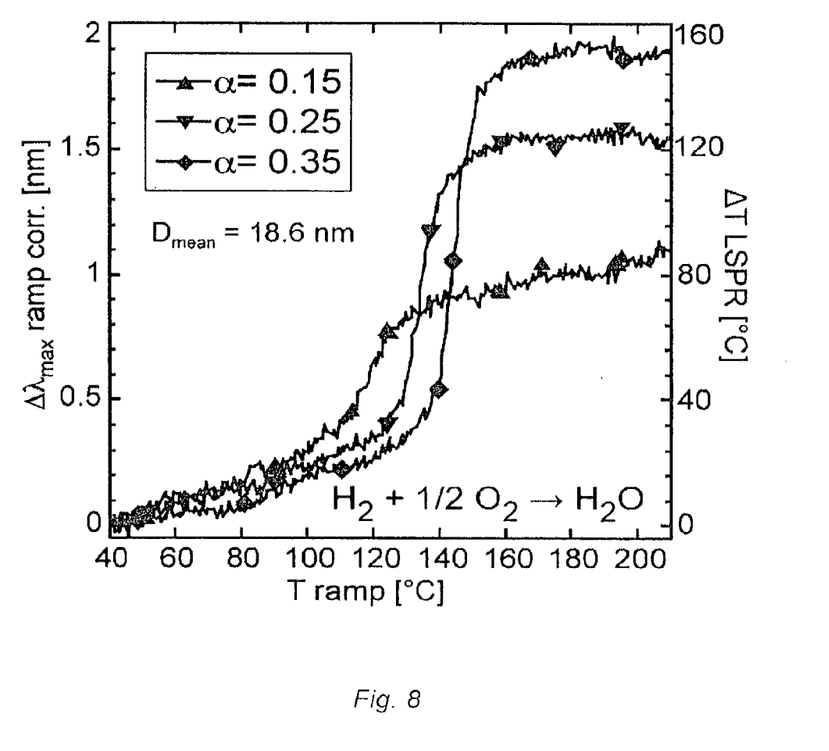
FIG. 8 is a graph showing catalytic light-off traces obtained for Pd nanoparticles with a mean diameter equal to 18.6 nm for three different relative $H_2$ and $O_2$ concentrations in Ar carrier gas.

FIG. 8 is a graph showings catalytic light-off traces (reactor heating-rate 4° C./min) obtained for Pd nanoparticles with a mean diameter equal to 18.6 nm for three different relative $H_2$ and $O_2$ concentrations in Ar carrier gas ($\alpha=[H_2]/([H_2]+[O_2])$). The displayed $\Delta\lambda_{max}$-values are corrected for the peak shift induced by external heating of the reactor (calibration curve in FIG. 7) and are caused by the local heat generated by the chemical reaction $H_2+{}^1AO_2 \rightarrow H_2O$ ($\Delta H=250$ kJ/mol) taking place on the Pd catalyst nanoparticles.

Figure 9:
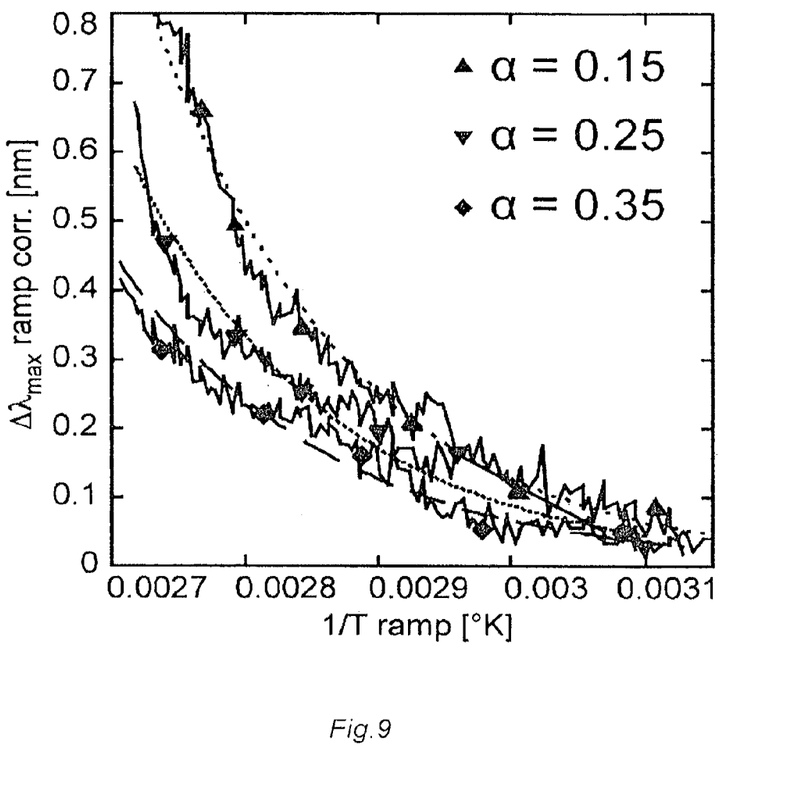
FIG. 9 is a graph showing an Arrhenius analysis of the low-temperature regime of the catalytic light-off traces for three different relative $H_2$ and $O_2$ concentrations in Ar carrier gas.

FIG. 9 is a graph showing an Arrhenius analysis of the low-temperature regime of the catalytic light-off traces shown in FIG. 8. The obtained apparent activation energies for three different reactant concentrations a are in excellent agreement with the literature.

Examples

Hydrogen Sensing

Indirect plasmonic sensors with Au nanodisks were fabricated on an optically transparent substrate using hole-mask colloidal lithography. The Au nanodisks were covered with a 10-30 nanometer (nm) thick $SiO_2$ separating layer. These Au nanodisks were thus the active sensor entity according to the indirect sensing scheme. The $SiO_2$ spacer served the purpose to physically separate the sensor nanoparticles from the studied nanoparticle entities (i.e. the sensing material). In this proof of concept experiment, palladium (Pd) particles having a diameter D=5 nm, formed after evaporation of a 1 nm thick, non-continuous granular film of Pd, were used as the sensing material. Note that for <10 nm Pd particles there is no LSPR excitations in the spectral range used here. The functioning of the sensor was tested by measuring hydrogen sorption/desorption isotherms at different temperatures and measuring optical extinction spectra for increasing and decreasing $H_2$ pressures. In FIG. 3 a series of absorption/desorption isotherms measured with Au nanodisks with a diameter D=120 nm and a height h=20 nm, covered with a 10 nm thick $SiO_2$ separating layer and a sensing material consisting of Pd nanoparticles with D=5 nm. The shift of the peak full-width-at-half maximum ($\Delta$fwhm) was monitored as a function of hydrogen pressure. Surprisingly, isotherms exhibiting the typical $\alpha$, $\alpha+\beta$, and $\beta$-phase regions were obtained. In the case of these small Pd nanoparticles both the observed slope of the $\alpha+\beta$ plateau and the enthalpy of hydride formation extracted from the data indicated that thermodynamics were no longer bulk like, as they were small enough to exhibit significant size effects in terms of their hydrogen storage capabilities.

Surprisingly, this measurement clearly shows that the sensitivity of the LSPR in the Au disks was sufficient, in spite of the presence of the separating layer, to detect the very small changes of the dielectric properties of the small Pd nanoparticles decorating the disks, when they were absorbing hydrogen both in the $\alpha$-phase and in the $\beta$/hydride phase. This makes this sensing approach highly useful to characterize nanoscopic hydrogen storage systems, in a size range between 1 and 10 nm, where thermodynamic and kinetic size effects can be expected. Surprisingly, experiments with calibration of the scaling of the optical response from this indirect LSPR sensor with hydrogen concentration in the sensing material by means of complementary experimental measurements using a Quartz Crystal Microbalance (QCM), suggest a linear dependence of the optical response with hydrogen concentration.

Nanoplasmonic NOx Sensing

Surprisingly, we have found a new type of optical $NO_x$ sensor, based on the indirect sensing scheme, that may be able to operate in harsh environments while at the same time allowing real time $NO_x$ detection with ultra-high sensitivity. The solution, in brief, comprises sensor nanoparticles, embedded in an oxide (e.g. BaO) whose dielectric properties change when $NO_x$ is bound into the oxide layer. In this particular example the bulk part of the oxide layer served as inert separation layer to protect the sensor nanoparticle from the harsh $NO_x$ environment. Only the outermost (towards the $NO_x$ environment) part of this oxide layer then interacted with the $NO_x$ and underwent chemical reaction. The chemical transformation gave rise to a change of the dielectric properties of the outermost region of the separation oxide layer.

The centerpiece of the proposed proof of concept sensor consisted of Au nanoparticles fabricated using hole-mask colloidal lithography on a transparent substrate, covered with a 20-100 nm thick BaO layer and Pt nanoparticles (diameter between 2 nm and 7 nm, i.e. 2 nm<D<7 nm) acting as a catalyst, covering an area of about 100 mm². A thin layer of BaO (30 nm in the example below) was evaporated over the Au nanoparticles creating a dielectric environment that, together with the Au nanoparticle geometry, determined the spectral position of the LSPR. The latter was measured in a simple optical experiment where white light impinged on the detector and the intensity of the signal transmitted through the detector structure was measured as a function of wavelength.

The functioning of the sensor was tested in a small flow reactor by exposing it to periodic cycles of $NO_2{}^+O_2$ and $H_2$. The operation conditions in the flow reactor mimicked some of the conditions in a car exhaust system: 230° C. operating temperature, 30-1000 part per million (ppm) $NO_2+6\%$ $O_2$ at a volume flow rate of 1000 ml/min was periodically cycled with 2% $H_2$ with the same volume flow. FIG. 4 shows the resulting reversible (upon $NO_x$ storage and release) shift in the LSPR signal of the Au sensor nanoparticles as function of time. FIG. 5a shows the resulting reversible shifts in LSPR of the Au sensor nanoparticles for exposures to different $NO_2$ concentrations in the carrier gas. The sample was exposed to hydrogen from zero to 8 minutes and from 38 minutes to 50 minutes. Between 8 minutes and 38 minutes the sample was exposed to 30-1000 ppm $NO_2$+6% $O_2$. The obtained periodicity in the LSPR peak shift was clearly related to the conversion of BaO to $Ba(NO_3)_2$ (and related species) as well as the reverse process. The surprisingly high sensitivity of the method is impressive since the total shift of the LSPR peak position was about 6 nm while the resolution in our optical measurements is almost a factor of 100 higher. The time response of the nitrate formation process was dictated by the kinetics of the reaction (both surface and bulk). FIG. 5b shows the dependence of the LSPR peak shift after 30 minutes (min.) of $NO_2$+$O_2$ exposure on the $NO_2$ concentration in the feed flow.

Nanoplasmonic Catalysis Sensing

Indirect plasmonic sensors with Au nanodisks (D=76 nm, h=30 nm, $\lambda_{max}$=570 nm) were fabricated using hole-mask colloidal lithography, on an optically transparent substrate. The Au nanodisks were covered with a 10 nanometer (nm) thick $SiO_2$ separating layer. These Au nanodisks were thus the active sensor nanoparticles according to the indirect sensing scheme. A 2 nm granular Pt film was deposited onto the $SiO_2$ layer and served as the sensing material. The deposited amount of Pt was so small that it resulted in individual Pt nanoparticles of sizes in the range 5-20 nm, mimicking the size range of real supported Pt catalysts. The transmission of white light through the sample was detected as a function of wavelength, using an array spectrometer.

We investigated the Pt-catalyzed oxidation of hydrogen The experiment was performed by slowly varying the relative $H_2$ concentration, $\alpha=[H_2]/([H_2]+[O_2])$, from hydrogen rich to oxygen rich and back again, while continuously recording $\lambda_{max}$ The sample temperature was measured with a thermocouple in contact with the sample surface The result is shown in FIG. 6 The reactant ($H_2$+$O_2$) concentration was kept constant at 4% in argon (Ar) carrier gas at atmospheric pressure, using a gas flow of 16 7 ml/s (3 4 cm/s plug flow velocity) The sample temperature T (measured in Kelvin K), without reaction, was 509 K The most surprising result is the discontinuous step up (down) in $\Delta\lambda_{max}$ at a critical reactant mixture of $\alpha_{cr}$=0 5 (the curves indicated with ▲ and T in FIG. 6) This step is completely absent in control measurements on an identical structure without Pt particles The step in $\Delta\lambda_{max}$ coincides with a peak ($\Delta T_{max}$=16 K) in the simultaneously measured sample temperature (curves indicated with V and Δ in FIG. 6), which is caused by the exothermicity of the reaction $\Delta\lambda_{max}$ varies only slowly above and below $\alpha_{cr}$ The data was corrected for a small background signal, caused by the interaction of reactant gases with the $SiO_2$ surface This correction did not affect the position or magnitude of the step in The $\Delta\lambda_{max}$ step is assigned to the well known kinetic phase transition in the $H_2$+$O_2$ reaction, occurring at a critical gas mixture, $\alpha_{cr}$, where a sudden transition occurs from an oxygen covered surface at low $\alpha$ to a partially hydrogen covered surface at high $\alpha$ This transition occurs, where the overall reaction has a rate maximum, which is the reason for the peak in temperature Since the kinetic phase transition at $\alpha=\alpha_{cr}$ involves a transition from an essentially oxygen saturated to a partially hydrogen covered surface, this example demonstrates that, surprisingly, LSPR can (ι) detect surface coverage changes at the submonolayer level on small supported Pt nanoparticles and (ιι) follow the kinetics of a catalytic reaction From this data and calibration data we estimate that LSPR can be used to monitor changes in adsorbate coverages on "realistic" supported catalysts with a sensitivity corresponding to (much) less than 0 1 monolayer of oxygen The slopes of the LSPR peak position, on both sides of the kinetic phase transition, are due to the reaction-induced temperature variation (exothermic reaction), which affects $\Delta\lambda_{max}$. This effect can be used to measure the heat generated (consumed) during a chemical/catalytic reaction.

Nanoplasmonic Temperature Sensing and Optical Calorimetry

Calorimetry on large volume catalyst systems and also micro-calorimetry are widely used for investigating catalytic reactions. Generally, one can determine the reaction rate as a function of temperature or reactant mixture and the overall rate maximum of a catalytic reaction, by measuring the energy dissipation (for exothermic reactions). Further, dissipated heat from an exothermic catalytic reaction is a critical parameter for phenomena like catalytic ignition and light-off in catalytic converters for e.g. car emission cleaning. Being able to perform calorimetry locally at the nanoscale with, potentially, single-particle resolution is therefore of great value for the catalysis and surface science community.

For a typical catalytic reaction, at low catalyst temperatures, when the reaction is slow enough not to be limited by mass transport, the reaction rate and the associated dissipated chemical power, are kinetically limited and commonly governed by Arrhenius-like kinetics. Upon further temperature increase the system reaches and passes through a transient regime where a transition takes place from kinetically controlled to mass transport controlled conditions (i.e. governed by concentration gradients), yielding a typical S-like curve of reaction rate versus temperature.

In the present example for an optical nano-calorimetric measurement, the chemical power generated by the exothermic $H_2^+O_2$ reaction on Pd nanoparticles deposited onto the indirect nanoplasmonic sensor (Au sensor nanodisks D=76 nm, h=30 nm, 10 nanometer (nm) thick $SiO_2$ separating layer) causes a temperature rise on the sample surface and of the sensing Au nanodisks, which causes a spectral shift of the LSPR peak. Via the latter and the calibrated temperature dependence of the Au LSPR peak (FIG. 7), the local temperature rise caused by the reaction is obtained, i.e. we establish a nano-calorimetric measurement.

FIG. 8 shows catalytic light-off traces (reactor heating-rate 4° C./min) obtained for Pd nanoparticles with <D>=18.6 nm for three different relative $H_2$ and $O_2$ concentrations in Ar carrier gas ($\alpha=[H_2]/([H_2]+[O_2])$). The displayed $\Delta\lambda_{max}$-values in FIG. 8 are corrected for the peak shift induced by external heating of the reactor (calibration curve in FIG. 7). If there was no other heating/power source than the external heating, the three curves, corresponding to three different $H_2$/$O_2$ mixtures ($\alpha$=0.15, 0.25 and 0.35), would all lie flat on the abscissa. The rise over the abscissa is attributed to an LSPR peak shift induced by local heating of the Au sensor nanodisks, due to the dissipated heat from the exothermic $H_2$+½$O_2$→$H_2O$ reaction ($\Delta H$=250 kJ/mol) on the Pd catalyst particles. The reaction induced T-rise increases with increasing reactor temperature ($T_{ramp}$), due to the Arrhenius type temperature dependence of the reaction.

The general form of the curves (for the three $\alpha$ values) is as expected from the general considerations above (S-curve); a first slow rise of temperature (i.e. of the reaction rate), until a fast rise begins (transition from kinetic limitation to mass transport limitation) and then a flattening, when the reaction reaches the mass transport limited regime, and therefore becomes rather insensitive to further temperature rise.

To quantify these measurements and demonstrate the direct correlation between measured LSPR shift and local catalyst temperature, an Arrhenius analysis of the low-temperature regime is shown in FIG. 9. The obtained apparent activation energies for three different reactant concentrations are in excellent agreement with the literature.

Generally the example above demonstrates that the (indirect) nanoplasmonic sensing offers a unique and generic nanocalorimethc way of studying catalytic reactions. We note that the general concept of this optical nano-calorimetry is directly extendable to common materials science techniques like differential scanning calorimetry (DSC), and will allow DSC measurements with extremely small sample amounts on the nano scale. We also note that the very local temperature measurement allowed by this approach can be combined on a single chip, in a multiplexing manner, and will then provide a more reliable local temperature measurement than average sample temperature measurements.

The invention claimed is:

1. An arrangement for indirect sensing in a surrounding environment, comprising at least one sensor nanoparticle, at least one sensing material and at least one separating layer which separates the at least one sensor nanoparticle from the at least one sensing material, wherein the at least one sensor nanoparticle supports a Localized Surface Plasmon Resonance, wherein said sensing material is placed on the separating layer on the opposite side of the separating layer from the at least one sensor nanoparticle so that the sensing material is separated from the sensor nanoparticle by the separating layer, wherein said separating layer is selected from the group consisting of transition metal oxides, semiconductor oxides, insulators, sulfides, nitrides, carbides, alkaline earth metal oxides, polymers and hydrogels, wherein the at least one sensor nanoparticle is physically protected and separated from the sensing material and the surrounding environment and does not interact with the sensing material or undergo change due to changes in the sensing material, but exhibits a change of Localized Surface Plasmon Resonance optical response upon a structural, chemical, refractive index, and/or electronic change of said sensing material upon interaction of the sensing material with the surrounding medium, wherein said sensing material is in a form selected from the group consisting of particles, nanoparticles, nanowires, nanofibers, nanotubes, a thin film and/or bulk material in solid, liquid or gas phase, and wherein said sensing material is selected from the group consisting of metals, metal oxides, transition metal oxides, sulfides, nitrides, carbides, alkaline earth metal oxides, polymers and hydrogels.

2. The arrangement according to claim 1, wherein the at least one sensor nanoparticle exhibits a change of Localized Surface Plasmon Resonance optical response upon a temperature change of a surrounding medium and/or the sensing material and/or the at least one sensor nanoparticle.

3. The arrangement according to claim 2, wherein the change of the optical response is at least one of spectral shift of the optical excitation, a change of optical cross section such as extinction, transmission, absorption, scattering or reflection, a change of spectral line width, and a change of the optical cross-section spectrally close to the optical excitation.

4. The arrangement according to claim 1, wherein said at least one sensor nanoparticle is a disk, rod, wire, ellipse, polygon, triangle, sphere, cube, star, hole in thin metal film, nanoshell, core-shell particle, nanorice or nanorings.

5. The arrangement according to claim 1, wherein the at least said one sensor nanoparticle comprises a metal.

6. The arrangement according to claim 5, wherein said metal is selected from Ag, Au, Cu, Al, Mg, Ni, Pd and Pt.

7. The arrangement according to claim 5, wherein said metal is selected from Sn, Hf, Ru, Rh, Ir, and Cr.

8. The arrangement according to claim 1, wherein said separating layer is a solid or a liquid.

9. The arrangement according to claim 1, wherein said separating layer has a thickness that is equal to or less than 1000 nm, 0.25-1000 nm, 400-1000 nm, 75-500 nm, 10-100 nm, 5-50 nm or 0.25-10 nm.

10. The arrangement according to claim 1, wherein said arrangement is located on a substrate or dispersed in soft or solid matter.

11. The arrangement according to claim 1, further comprising control and measurement electronics, computational devices and/or physical detectors.

12. A method of indirect sensing in a surrounding environment, comprising using an arrangement comprising at least one sensor nanoparticle, at least one sensing material, and at least one separating layer that separates the at least one sensor nanoparticle from the at least one sensing material, wherein the at least one sensor nanoparticle supports a Localized Surface Plasmon Resonance, wherein said sensing material is placed on the separating layer on the opposite side of the separating layer from the at least one sensor nanoparticle so that the sensing material is separated from the sensor nanoparticle by the separating layer, wherein said separating layer is selected from the group consisting of transition metal oxides, semiconductor oxides, insulators, sulfides, nitrides, carbides, alkaline earth metal oxides, polymers and hydrogels, wherein the at least one sensor nanoparticle is physically protected and separated from the sensing material and the surrounding environment and does not interact with the sensing material or undergo change due to changes in the sensing material, but exhibits a change of Localized Surface Plasmon Resonance optical response upon a structural, chemical, refractive index, and/or electronic change of said sensing material upon interaction of the sensing material with the surrounding medium, wherein said sensing material is in a form selected from the group consisting of particles, nanoparticles, nanowires, nanofibers, nanotubes, a thin film and/or bulk material in solid, liquid or gas phase, and wherein said sensing material is selected from the group consisting of metals, metal oxides, transition metal oxides, sulfides, nitrides, carbides, alkaline earth metal oxides, polymers and hydrogels.

13. The method of claim 12, wherein the arrangement is used for surface enhanced Raman scattering spectroscopy and/or surface enhanced infrared absorption spectroscopy.

14. The method of claim 12, wherein the arrangement is used for optical differential scanning calorimetry.

15. The method of claim 12, wherein the arrangement is used for hydrogen storage, hydrogen sensing, catalytic reaction sensing or $NO_x$ sensing.

16. An arrangement in a surrounding environment comprising at least one sensor nanoparticle, and at least one separating layer that separates the at least one sensor nanoparticle from a surrounding medium, wherein the at least one sensor nanoparticle supports a Localized Surface Plasmon Resonance, and wherein a surface of the separating layer facing the surrounding medium is arranged to support a sensing material deposited on the surface of the separating layer on the opposite side of the separating layer from the at least one sensor nanoparticle so that the sensing material is separated from the sensor nanoparticle by the separating layer, wherein said separating layer is selected from the group consisting of transition metal oxides, semiconductor oxides, insulators, sulfides, nitrides, carbides, alkaline earth metal oxides, polymers and hydrogels, wherein the at least one sensor nanoparticle is physically protected and separated from the sensing material and the surrounding environment and does not interact with the sensing material or undergo change due to changes in the sensing material, but exhibits a chance of Localized Surface Plasmon Resonance optical response upon a structural, chemical, refractive index, and/or electronic change of said sensing material upon interaction of the sensing material with the surrounding medium.

* * * * *